(12) United States Patent
Brighton (10) Patent No.: US 8,017,369 B2
(45) Date of Patent: *Sep. 13, 2011

(54) SYSTEM AND METHOD OF UP-REGULATING BONE MORPHOGENETIC PROTEINS (BMP) GENE EXPRESSION IN BONE CELLS VIA THE APPLICATION OF FIELDS GENERATED BY SPECIFIC AND SELECTIVE ELECTRIC AND ELECTROMAGNETIC SIGNALS

(75) Inventor: Carl T Brighton, Malvern, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 936 days.

This patent is subject to a terminal disclaimer.

(21) Appl. No.: 10/585,718

(22) PCT Filed: Jan. 11, 2005

(86) PCT No.: PCT/US2005/000793
§ 371 (c)(1),
(2), (4) Date: Jan. 9, 2007

(87) PCT Pub. No.: WO2005/070136
PCT Pub. Date: Aug. 4, 2005

(65) Prior Publication Data
US 2007/0299472 A1    Dec. 27, 2007

Related U.S. Application Data

(63) Continuation-in-part of application No. 10/257,126, filed as application No. PCT/US01/05991 on Feb. 23, 2001, now Pat. No. 7,465,566.

(60) Provisional application No. 60/184,491, filed on Feb. 23, 2000, provisional application No. 60/535,755, filed on Jan. 12, 2004.

(51) Int. Cl.
*C12N 13/00* (2006.01)
(52) U.S. Cl. ........................ 435/173.8; 607/51
(58) Field of Classification Search ................ None
See application file for complete search history.

(56) References Cited

U.S. PATENT DOCUMENTS

| | | | |
|---|---|---|---|
| 4,430,999 A | 2/1984 | Brighton et al. | 128/419 |
| 4,442,846 A | 4/1984 | Brighton et al. | 128/784 |
| 4,467,808 A | 8/1984 | Brighton et al. | 128/419 F |
| 4,467,809 A | 8/1984 | Brighton | 607/51 |
| 4,487,834 A | 12/1984 | Brighton | 435/173 |
| 4,506,674 A | 3/1985 | Brighton et al. | 128/419 |
| 4,509,520 A | 4/1985 | Dugot | 128/419 |
| 4,535,775 A | 8/1985 | Brighton et al. | 128/419 |
| 4,549,547 A | 10/1985 | Brighton et al. | 128/419 F |
| 4,600,010 A | 7/1986 | Dugot | 128/419 |
| 4,683,873 A | 8/1987 | Cadossi et al. | 128/1.5 |
| 5,014,699 A | 5/1991 | Pollack et al. | 128/419 |
| 5,038,797 A | 8/1991 | Batters | 128/798 |
| 5,269,746 A | 12/1993 | Jacobson | 600/13 |
| 5,273,033 A | 12/1993 | Hoffman | 607/46 |
| 5,338,286 A | 8/1994 | Abbott et al. | 600/14 |
| 5,374,283 A | 12/1994 | Flick | 607/46 |
| 5,743,844 A | 4/1998 | Tepper et al. | 600/14 |
| 5,968,527 A | 10/1999 | Litovitz | 424/400 |
| 6,083,149 A | 7/2000 | Wascher et al. | 600/9 |
| 6,132,362 A | 10/2000 | Tepper et al. | 600/14 |
| 6,186,940 B1 | 2/2001 | Kirschbaum | 600/12 |
| 6,261,221 B1 | 7/2001 | Tepper et al. | 600/14 |
| 6,292,699 B1 | 9/2001 | Simon et al. | 607/51 |
| 6,485,963 B1 | 11/2002 | Wolf et al. | 435/298.2 |
| 6,605,089 B1 | 8/2003 | Michelson | 606/61 |
| 6,747,004 B1 | 6/2004 | Tabibzadeh | 514/12 |
| 7,022,506 B2 | 4/2006 | Brighton et al. | |
| 7,130,692 B2 * | 10/2006 | Brighton et al. | 607/50 |
| 7,215,995 B2 * | 5/2007 | Brighton et al. | 607/2 |

(Continued)

FOREIGN PATENT DOCUMENTS

EP        0 652 028 A1     5/1995

(Continued)

OTHER PUBLICATIONS

Bodamyali, T et al., "Pulsed electromagnetic fields simultaneously induce osteogenesis and upregulate transcription of bone morphogenetic proteins 2 and 4 in rat osteoblasts in vitro," Biochem Biophys Res Commun, Sep. 18, 1998, 250 (2), 458-461.

(Continued)

*Primary Examiner* — Jim Ketter
(74) *Attorney, Agent, or Firm* — Woodcock Washburn, LLP (57) ABSTRACT

Methods and devices are described for the regulation of bone morphogenetic protein gene expression in bone cells via the application of fields generated by specific and selective electric and electromagnetic signals in the treatment of diseased or injured bone. By gene expression is meant the up-regulation or down-regulation of the process whereby specific portions (genes) of the human genome (DNA) are transcribed into mRNA and subsequently translated into protein. Methods and devices are provided for the targeted treatment of injured or diseased bone tissue that include generating specific and selective electric and electromagnetic signals that generate fields optimized for increase of bone morphogenetic protein gene expression and exposing bone to the fields generated by specific and selective signals so as to regulate bone morphogenetic protein gene expression in such bone tissue. The resulting methods and devices are useful for the targeted treatment of bone fractures, fractures at risk, delayed unions, nonunion of fractures, bone defects, spine fusions, osteonecrosis or avascular necrosis, as an adjunct to other therapies in the treatment of one or all of the above, and in the treatment of osteoporosis.

24 Claims, 8 Drawing Sheets

U.S. PATENT DOCUMENTS

| | | | |
|---|---|---|---|
| 7,374,916 B2 * | 5/2008 | Brighton | 435/173.8 |
| 7,429,471 B2 * | 9/2008 | Brighton | 435/173.8 |
| 7,465,546 B2 * | 12/2008 | Brighton | 435/6 |
| 7,465,566 B2 * | 12/2008 | Brighton et al. | 435/173.8 |
| 2002/0038137 A1 | 3/2002 | Stein | |
| 2002/0052634 A1 | 5/2002 | March | 607/50 |
| 2003/0211084 A1 | 11/2003 | Brighton et al. | 424/93.7 |
| 2004/0138709 A1 | 7/2004 | Brighton | |
| 2005/0049640 A1 | 3/2005 | Gurtner et al. | |

FOREIGN PATENT DOCUMENTS

| | | |
|---|---|---|
| EP | 1 198 580 B1 | 5/2006 |
| RU | 2147895 C1 | 4/2000 |
| WO | WO 00/02585 A1 | 1/2000 |
| WO | WO 01/62336 A1 | 8/2001 |
| WO | WO 2004/029210 | 4/2004 |
| WO | WO 2005/070136 A2 | 8/2005 |

OTHER PUBLICATIONS

Brighton, C.T., "Present and Future of Electrically Induced Osteogenesis," Clinical Trends in Orthopaedics, Jan. 1, 1981, 1-15.

Aaron, R.K., et al., "The conservative treatment of osteonecrosis of the femoral head," Clin. Orthop., 1989, 249, 209-218.

Aaron, R.K., et al., "Stimulation of experimental endochondral ossification by low-energy pulsing electromagnetic fields," J. Bone Miner. Res., Nov. 2, 1989, 4, 227-233.

Bassett,C.A.L., "Low energy pulsing electromagnetic fields modify biomedical processes," BioEssays, 1987, 6(1), 36-42.

Bassett, C.A.L., et al., "Effects of pulsed electromagnetic fields on Steinberg ratings of femoral head osteonecrosis," Clin. Orthop., Sep. 1989, 246, 172-185.

Bassett, C.A.L., et al., "Fundamental and practical aspects of therapeutic uses of pulsed electromagnetic fields (PEMSs)," Crit. Rev. Biomed. Eng., 1989, 17(5), 451-529.

Bassett, C.A.L., et al., "Pulsing electromagnetic field treatment in ununited fractures and failed arthrodeses," JAMA, Feb. 5, 1982, 247(5), 623-628.

Binder, A., et al., "Pulsed electromagnetic field therapy of persistent rotator cuff tendonitis," Lancet, Mar. 31, 1984, 695-698.

Brighton, C.T., et al., "A multicenter study of the treatment of nonunion with constant direct current," J. Bone and Joint Surgery, Jan. 1981, 62-A(1), 2-13.

Brighton, C.T., et al., "Treatment of recalcitrant non-union with a capacitively coupled electrical field," J. Bone and Joint Surgery, Apr. 1985, 67-A(4), 577-585.

Brighton, C.T., et al., "Treatment of castration-induced osteoporosis by a capacitively coupled electrical signal in rat vertebrae," J. Bone and Joint Surgery, Feb. 1989, 71-A(2), 228-236.

Brighton, C.T., et al., "Increased cAMP production after short-term capacitively coupled stimulation in bovine growth plate chondrocytes," J. Orthop. Res., 1988, 6, 552-558.

Brighton, C.T., et al., "Treatment of denervation/disuse osteoporosis in the rat with a capacitively coupled electrical signal: effects on bone formation and bone resorption," J. Orthop. Res., 1988, 6, 676-684.

Brighton, C.T., et al., "Fracture healing in the rabbit fibula when subjected to various capacitively coupled electrical fields," J. Orthop. Res., 1985, 3, 331-340.

Brighton, C.T., et al., "In vitro bone-cell response to a capacitively coupled electrical field," Clin. Orthop. Related Res., Dec. 1992, 285, 255-262.

Brighton, C.T., et al., "Signal transduction in electrically stimulated bone cells," J. Bone Joint Surg. Am., 2001, 83-A(10), 1514-1523.

Carter, E.L., et al., "Field distributions in vertebral bodies of the rat during electrical stimulation: a parametric study," IEEE Trans. on Biomed. Eng., Mar. 1989, 36(3), 333-345.

Goodman, R., et al., "Exposure of salivary gland cells to low-frequency electromagnetic fields alters polypeptide synthesis," Proc. Natl. Acad. Sci. USA, Jun. 1988, 85, 3928-3932.

Goodwin, C.B., et al., "A double-blind study of capacitively coupled electrical stimulation as an adjunct to lumbar spinal fusions," Spine, 1999, 24(13), 1349-1356.

Grodzinsky, A.J., "Electromechanical and physicochemical properties of connective tissue," Crit. Rev. Biomed. Engng., 1983, 9(2), 133-198.

Harrison, M.H.M., et al., "Use of pulsed electromagnetic fields in perthes disease: report of a pilot study," J. Pediatr. Orthop., 1984, 4, 579-584.

Jones, D.B., et al., "PEMF effects on differentiation and division in mirine melanoma cells are mediated indirectly through cAMP," Trans. BRAGS 6, 1986, 51.

Lorich, D.G., et al., "Biochemical pathway mediating the response of bone cells to capacitive coupling," Clin. Orthop. and Related Res., 1998, 350, 246-256.

Massaro, L., et al., "Osteoarthritis of the knee joint: an eight year prospective study," Ann Rheum Dis., 1989, 48, 893-897.

Mooney, V., "A randomized double-blind prospective study of the efficacy of pulsed electromagnetic fields for inter body lumbar fusions," Spine, 1990, 15(7), 708-712.

Norton, L.A., et al., "Pulsed electromagnetic fields alter phenotypic expression in chondroblasts in tissue culture," J. Orthop. Res., 1988, 6, 685-689.

Pienkowski, D., et al., "Low-power electromagnetic stimulation of osteotomized rabbit fibuiae," J. of Bone & Joint Surgery, 1994, 76-A(4), 489-501.

Rodan, G.A., et al., "DNA synthesis in cartilage cells is stimulated by oscillating electric fields," Science, Feb. 10, 1978, 199, 690-692.

Ryaby, J.T., et al., "Pulsing electromagnetic fields affect the phosphorylation and expression of oncogene proteins," Trans. BRAGS 6, 1986, p. 78.

Ryaby, J.T., et al., "The effect of electromagnetic fields on protein phosphorylation and synthesis in murine melanoma cells," BRAGS, p. 32, (1986).

Wang, W., et al., "The increased level of PDGF-A constributes to the increased proliferation induced by mechanical stimulation in osteoblastic cells," Biochem. and Molecular Biol. International, Oct. 1997, 43(2), 339-346.

Wang, W., et al., "Up-regulation of chondrocyte matrix genes and products by electric fields," Clin. Orthopaedics & Related Res., 427S, S163-S173, (2004).

Zhuang, H., et al., "Mechanical strain-induced proliferation of osteoblastic cells parallels increased TGF-$\beta$1 mRNA," Biochem. Biophys. Res. Commun., 1996, 229, 449-453.

Zhuang, H., et al., "Electrical stimulation induces the level of TGF-$\beta$1 mRNA in osteoblastic cells by a mechanism involving calcium/calmodulin pathway," Biochem. Biophys. Res. Commun., 1997, 237, 225-229.

Brighton, C.T., et al., "Prevention and treatment of sciatic denervation disuse osteoporosis in rat tibia with capacitively coupled electrical stimulation," Bone, 1985, 6, 87-97.

Brighton, C.T., et al., "Treatment of nonunion of the tibia with a capacitively coupled electrical field," J. of Trauma, 1984, 24(2), 153-155.

Brighton, C.T., et al., "Tibial nonunion treated with direct current, capacitive coupling, or bone graft," Clin. of Orthop. and Related Res., 1995, 321, 223-234.

\* cited by examiner

SYSTEM AND METHOD OF UP-REGULATING BONE MORPHOGENETIC PROTEINS (BMP) GENE EXPRESSION IN BONE CELLS VIA THE APPLICATION OF FIELDS GENERATED BY SPECIFIC AND SELECTIVE ELECTRIC AND ELECTROMAGNETIC SIGNALS

CROSS-REFERENCE TO RELATED APPLICATIONS

This application is the National Stage of International Application No. PCT/US2005/000793, filed Jan. 11, 2005, which is a continuation-in-part patent application of U.S. patent application Ser. No. 10/257,126, which is the U.S. national phase patent application of PCT/US01/05991, filed Feb. 23, 2001, which, in turn, claims the benefit of the filing date of U.S. Provisional Application No. 60/184,491, filed Feb. 23, 2000, and U.S. Provisional Patent Application No. 60/535,755, filed Jan. 12, 2004. The contents of these patent applications are hereby incorporated by reference in their entireties.

FIELD OF THE INVENTION

The present invention is directed to a method of up-regulating bone morphogenetic protein (BMP) gene expression in bone cells via the application of fields generated by specific and selective electric and electromagnetic signals for the treatment of injured or diseased bone, as well as devices for generating such signals.

BACKGROUND OF THE INVENTION

The bioelectrical interactions and activity believed to be present in a variety of biological tissues and cells are one of the least understood of the physiological processes. However, there has recently been much research into these interactions and activity regarding the growth and repair of certain tissues and cells. In particular, there has been much research into stimulation by electric and electromagnetic fields and its effect on the growth and repair of bone and cartilage. Researchers believe that such research might be useful in the development of new treatments for a variety of medical problems.

In the disease commonly known as osteoporosis, bone demineralizes and becomes abnormally rarefied. Bone comprises an organic component of cells and matrix as well as an inorganic or mineral component. The cells and matrix comprise a framework of collagenous fibers that is impregnated with the mineral component of calcium phosphate (85%) and calcium carbonate (10%) that imparts rigidity to the bone. While osteoporosis is generally thought as afflicting the elderly, certain types of osteoporosis may affect persons of all ages whose bones are not subject to functional stress. In such cases, patients may experience a significant loss of cortical and cancellous bone during prolonged periods of immobilization. Elderly patients are known to experience bone loss due to disuse when immobilized after fracture of a bone, and such bone loss may ultimately lead to a secondary fracture in an already osteoporotic skeleton. Diminished bone density may lead to vertebrae collapse, fractures of hips, lower arms, wrists, ankles as well as incapacitating pains. Alternative nonsurgical therapies for such diseases are needed.

Pulsed electromagnetic fields (PEMF) and capacitive coupling (CC) have been used widely to treat nonhealing fractures (nonunion) and related problems in bone healing since approval by the Food and Drug Administration in 1979. The original basis for the trial of this form of therapy was the observation that physical stress on bone causes the appearance of tiny electric currents that, along with mechanical strain, were thought to be the mechanisms underlying transduction of the physical stresses into a signal that promotes bone formation. Along with direct electric field stimulation that was successful in the treatment of nonunion, noninvasive technologies using PEMF and capacitive coupling (where the electrodes are placed on the skin in the treatment zone) were also found to be effective. PEMFs generate small, induced currents (Faraday currents) in the highly-conductive extracellular fluid, while capacitive coupling directly causes currents in the tissues; both PEMFs and CC thereby mimic endogenous electrical currents.

The endogenous electrical currents, originally thought to be due to phenomena occurring at the surface of crystals in the bone, have been shown to be due primarily to movement of fluid containing electrolytes in channels of the bone containing organic constituents with fixed negative charges, generating what are called "streaming potentials." Studies of electrical phenomena in bone have demonstrated a mechanical-electrical transduction mechanism that appears when bone is mechanically compressed, causing movement of fluid and electrolytes over the surface of fixed negative charges in the proteoglycans and collagen in the bone matrix. These streaming potentials serve a purpose in bone, and, along with mechanical strain, lead to signal transduction that is capable of stimulating bone cell synthesis of a calcifiable matrix, and, hence, the formation of bone.

The main application of direct current, capacitive coupling, and PEMFs has been in orthopedics in healing of nonunion bone fractures (Brighton et al., *J. Bone Joint Surg.* 63: 2-13, 1981; Brighton and Pollack, *J. Bone Joint Surg.* 67: 577-585, 1985; Bassett et al., *Crit. Rev. Biomed. Eng.* 17: 451-529, 1989; Bassett et al., *JAMA* 247: 623-628; 1982). Clinical responses have been reported in avascular necrosis of hips in adults and Legg-Perthes's disease in children (Bassett et al., *Clint. Orthop.* 246: 172-176, 1989; Aaron et al., *Clin. Orthop.* 249: 209-218, 1989; Harrison et al., *J. Pediatr. Orthop.* 4: 579-584, 1984). It has also been shown that PEMFs (Mooney, *Spine* 15: 708-712, 1990) and capacitive coupling (Goodwin, Brighton et al., *Spine* 24: 1349-1356, 1999) can significantly increase the success rate of lumbar fusions. There are also reports of augmentation of peripheral nerve regeneration and function and promotion of angiogenesis (Bassett, *Bioessays* 6: 36-42, 1987). Patients with persistent rotator cuff tendonitis refractory to steroid injection and other conventional measures, showed significant benefit compared with placebo-treated patients (Binder et al., *Lancet* 695-698, 1984). Finally, Brighton et al. have shown in rats the ability of an appropriate capacitive coupling electric field to both prevent and reverse vertebral osteoporosis in the lumbar spine (Brighton et al., *J. Orthop. Res.* 6:. 676-684, 1988; Brighton et al., *J. Bone Joint Surg.* 71: 228-236, 1989).

More recently, research in this area has focused on the effects stimulation has on tissues and cells. For example, it has been conjectured that direct currents do not penetrate cellular membranes, and that control is achieved via extracellular matrix differentiation (Grodzinsky, *Crit. Rev. Biomed. Eng.* 9:133-199, 1983). In contrast to direct currents, it has been reported that PEMFs can penetrate cell membranes and either stimulate them or directly affect intracellular organelles. An examination of the effect of PEMFs on extracellular matrices and in vivo endochondral ossification found increased synthesis of cartilage molecules and maturation of bone trabeculae (Aaron et al., *J. Bone Miner. Res.* 4: 227-233, 1989). More recently, Lorich et al. (*Clin. Orthop. Related Res.* 350: 246-256, 1998) and Brighton et al. (*J. Bone Joint Surg.* 83-A, 1514-1523, 2001) reported that signal transduction of a capacitively coupled electric signal is via voltage gated calcium channels, whereas signal transduction of PEMFs or combined electromagnetic fields is via the release of calcium from intracellular stores. In all three types of electrical stimulation there is an increase in cytosolic calcium with a subsequent increase in activated (cytoskeletal) calmodulin.

It was reported in 1996 by the present inventors that a cyclic biaxial 0.17% mechanical strain produces a significant increase in TGF-$\beta_1$ mRNA in cultured MC3T3-E1 bone cells (Brighton et al., *Biochem. Biophys. Res. Commun.* 229: 449-453, 1996). Several significant studies followed in 1997. In one study it was reported that the same cyclic biaxial 0.17% mechanical strain produced a significant increase in PDGF-A mRNA in similar bone cells (Brighton et al., *Biochem. Biophys. Res. Commun.* 43: 339-346, 1997). It was also reported that a 60 kHz capacitively coupled electric field of 20 mV/cm produced a significant increase in TGF-$\beta_1$ in similar bone cells (Brighton et al., *Biochem. Biophys. Res. Commun.* 237: 225-229, 1997). However, the effect such a field would have on other genes has not been reported in the literature.

In the above-referenced parent patent application, entitled Regulation of Genes Via Application of Specific and Selective Electrical and Electromagnetic Signals, methods were disclosed for determining the specific and selective electrical and electromagnetic signals for use in creating fields for regulating target genes of diseased or injured tissues. The present invention builds upon the technique described therein by describing the method of regulating expression of one targeted gene family, namely, bone morphogenetic protein(s) gene expression, through application of a field generated by a specific and selective electrical and electromagnetic signal, for the treatment of fresh fractures, fractures at risk, delayed unions, nonunion of fractures, bone defects, spine fusions, osteonecrosis or avascular necrosis, as an adjunct to other therapies in the treatment of one or all of the above, and in the treatment of osteoporosis.

SUMMARY OF THE INVENTION

The present invention relates to regulating bone morphogenetic protein gene expression in bone cells via the application of fields generated by specific and selective electric and/or electromagnetic signals. By performing dose-response curves on the electric field duration, amplitude, frequency, and duty cycle, the optimal signal for up-regulating bone morphogenetic protein mRNA in bone cells was discovered. The optimal signal generated a capacitively coupled electric field with an amplitude of 20 mV/cm, a duration of 24 hours, a frequency of 60 kHz, a duty cycle of 50%, and a sine wave configuration. In particular, the present invention relates to up-regulating bone morphogenetic protein (BMP) gene expression in bone cells via the application of fields generated by such signals.

In accordance with the invention, methods are provided to specifically and selectively up-regulate the gene expression (as measured by mRNA) of BMP-2, BMP-4, BMP-5, BMP-6, and BMP-7, with capacitively coupled electric fields, electromagnetic fields, or combined fields. Fresh fractures, fractures at risk, delayed unions, nonunion fractures, bone defects, osteonecrosis, osteoporosis, and the like are treated with a capacitively coupled electric field of about 20 mV/cm with an electric field duration of about 24 hours, a frequency of 60 kHz, a duty cycle of about 50%, and a sine wave configuration that causes the expression of BMP-2, BMP-4, BMP-5, BMP-6, and BMP-7 mRNAs to be up-regulated. In accordance with the method of the invention, a "specific and selective" signal is a signal that has predetermined characteristics of amplitude, duration, duty-cycle, frequency, and waveform that up-regulates the expression of the BMP genes (specificity). This allows one to choose different signals to up-regulate BMP gene expressions in order to achieve a given biological or therapeutic response (selectivity). The invention further relates to devices employing the methods described herein to generate specific and selective signals that create fields to up-regulate the expression of BMP genes.

In related aspects, the present invention relates to methods and devices for the treatment of fresh fractures, fractures at risk, delayed unions, nonunions, bone defects, spine fusion, osteonecrosis, as an adjunct to other therapies treating one or more of the above, and in the treatment of osteoporosis. The method of the invention also includes the methodology for determining the "specific and selective" signal for BMP gene expression by methodically varying the duration of a starting signal known to increase, or suspected to increase, cellular production of BMPs. After finding the optimal duration, the amplitude of the signal is varied for the optimal duration of time as determined by the gene expression of BMP-2, BMP4, BMP-5, BMP-6, and BMP-7. The duty cycle, frequency, and waveform are varied methodically in the same dose response manner as above while keeping the other signal characteristics constant. This process is repeated until the optimal signal is determined that produces the greatest increase in the expression of BMPs.

These and other aspects of the present invention will be elucidated in the following detailed description of the invention.

BRIEF DESCRIPTION OF THE DRAWINGS

The present invention will be apparent from the following detailed description of the invention taken in conjunction with the accompanying drawings, of which.

DETAILED DESCRIPTION OF ILLUSTRATIVE EMBODIMENTS

The invention will be described in detail below with reference to FIGS. 1-8. Those skilled in the art will appreciate that the description given herein with respect to those figures is for exemplary purposes only and is not intended in any way to limit the scope of the invention. All questions regarding the scope of the invention may be resolved by referring to the appended claims.

The present invention is based on the discovery that the expression of certain genes can be regulated by the application of fields generated by specific and selective electric and/or electromagnetic signals. In other words, it has been discovered by the present inventors that there is a specific electric and/or electromagnetic signal that generates a field for regulating each gene in bone, cartilage and other tissue cells and that these specific signals are capable of specifically and selectively regulating the genes in such cells. In particular, gene expression governing the growth, maintenance, repair, and degeneration or deterioration of tissues or cells can be regulated in accordance with the invention via the application of fields generated by specific and selective electric and/or electromagnetic signals so as to produce a salutary clinical effect. Such discoveries are useful in the development of treatment methods that target certain medical conditions including fresh bone fractures, fractures at risk, delayed union, nonunion, bone defects, osteonecrosis, as an adjunct in the treatment of any one or more of the above, and in the treatment of osteoporosis.

As used herein, the phrase "signal" is used to refer to a variety of signals including mechanical signals, ultrasound signals, electromagnetic signals and electric signals output by a device. It is to be understood that the term "field" as used herein refers to an electrical field within targeted tissue, whether it is a combined field or a pulsed electromagnetic field or generated by direct current, capacitive coupling or inductive coupling.

The phrase "remote" is used to mean acting, acted on or controlled from a distance. "Remote" regulation refers to controlling the expression of a gene from a distance. To provide "remotely" refers to providing from a distance. For example, providing a specific and selective signal from a remote source can refer to providing the signal from a source at a distance from a tissue or a cell, or from a source outside of or external to the body.

The phrase "specific and selective" signal means a signal that produces an electric field that has predetermined characteristics of amplitude, duration, duty cycle, frequency, and waveform that up-regulate or down-regulate a targeted gene or targeted functionally of complementary genes (specificity). This allows one to choose different "specific and selective" signals to up-regulate or down-regulate expression of various genes in order to achieve a given biological or therapeutic response (selectivity).

The term "regulate" means to control gene expression. Regulate is understood to include both up-regulate and down-regulate. Up-regulate means to increase expression of a gene, while down-regulate means to inhibit or prevent expression of a gene.

"Functionally complementary" refers to two or more genes whose expressions are complementary or synergistic in a given cell or tissue.

"Tissue" refers to an aggregate of cells together with their extracellular substances that form one of the structural materials of a patient. As used herein, the term "tissue" is intended to include muscle and organ tissue, tumor tissue as well as bone or cartilage tissue. Also, the term "tissue" as used herein may also refer to an individual cell.

"Patient" refers to an animal, preferably a mammal, more preferably a human.

The present invention provides treatment methods and devices that target certain tissues, cells or diseases. In particular, the gene expression associated with the repair process in injured or diseased tissues or cells can be regulated by the application of fields generated by electric signals that are specific and selective for the genes to be regulated in the target tissues or cells. Gene expression can be up-regulated or down-regulated by the application of signals that are specific and selective for each gene or each set of complementary genes so as to produce a beneficial clinical effect. For example, a particular specific and selective signal may create an electric field that up-regulates a certain desirable gene expression, while the same or another particular specific and selective signal may create an electric field that down-regulates a certain undesirable gene expression. A certain gene may be up-regulated by a field generated by one particular specific and selective signal and down-regulated by a field generated by another specific and selective signal. Those skilled in the art will understand that certain diseased or injured tissues can be targeted for treatment by regulating those genes governing the growth, maintenance, repair, and degeneration or deterioration of the tissues.

The methods and devices of the present invention are based on identifying those signals that generate fields that are specific and selective for the gene expression associated with certain targeted diseased or injured tissue. For example, electricity in its various forms (e.g., capacitive coupling, inductive coupling, combined fields) can specifically and selectively regulate gene expression in targeted tissues or cells in a patient's body by varying the frequency, amplitude, waveform or duty cycle of the applied field for each selected gene. The duration of time exposed to electricity can also influence the capability of electricity to specifically and selectively regulate gene expression in targeted tissues or cells in a patient's body. Specific and selective signals may generate electric fields for application to each gene systematically until the proper combination of frequency, amplitude, waveform, duty cycle, and duration is found that provides the desired effect on gene expression.

It is to be understood that a variety of diseased or injured tissues or disease states can be targeted for treatment because the specificity and selectivity of an electric field for a certain gene expression can be influenced by several factors. In particular, an electrical field of appropriate frequency, amplitude, waveform and/or duty cycle can be specific and selective for the expression of certain genes and thus provide for targeted treatments. Temporal factors (e.g., duration of time exposed to the electrical field) can also influence the specificity and selectivity of an electric field for a particular gene expression. The regulation of gene expression may be more effective (or made possible) via the application of an electrical field for a particular duration of time. Therefore, those skilled in the art will understand that the present invention provides for varying the frequency, amplitude, waveform, duty cycle and/or duration of application of an electric field until the electric field is found to be specific and selective for certain gene expressions in order to provide for treatments targeting a variety of diseased or injured tissue or diseases.

Thus, the present invention can provide for targeted treatments because it is possible to regulate expression of certain genes associated with a particular diseased or injured tissue via the application of fields generated by specific and selective signals of appropriate frequency, amplitude, waveform and/or duty cycle for an appropriate duration of time. The specificity and selectivity of a signal generating an electrical field may thus be influenced so as to regulate the expression of certain genes in order to target certain diseased or injured tissue or disease states for treatment. In particular, the present invention provides for the targeted treatment of fresh bone fractures, fractures at risk, nonunion, bone defects, spine fusion, osteonecrosis, as an adjunct in the treatment of one or any of the above, and in the treatment of osteoporosis.

The present invention also provides a device that includes a source of at least one signal specific and selective for BMP gene expression. The devices of the present invention can provide for the production of such signals for application to bone cells by at least one electrode adapted to apply the field generated by the specific and selective signal.

Figure 8:
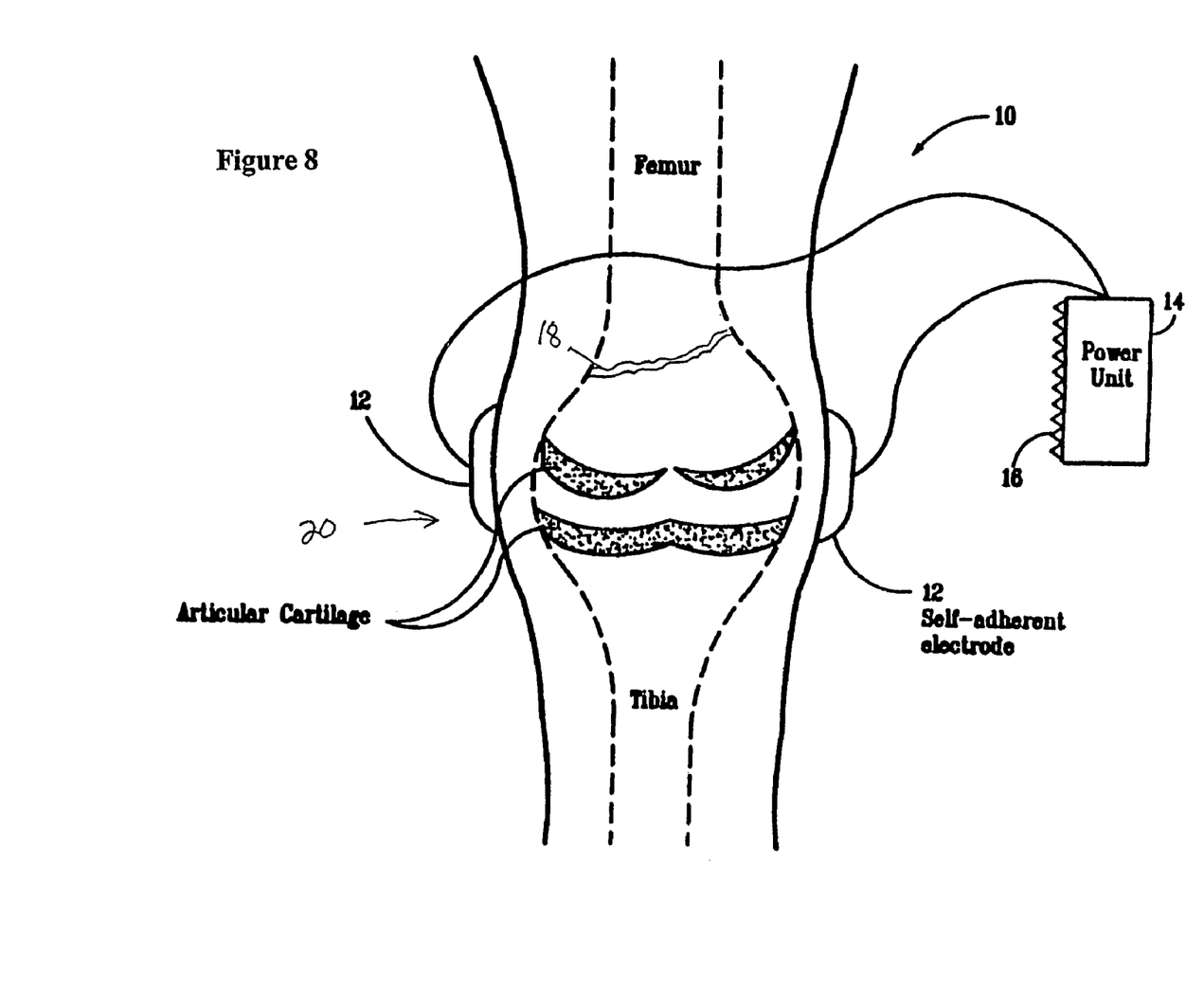
FIG. 8 is a diagram illustrating a device for up-regulating the gene expression of bone morphogenetic protein, in accordance with an exemplary embodiment of the present invention.

The devices of the present invention are capable of applying a field generated by specific and selective signals directly to diseased or injured tissue, bone and/or to the skin of a patient. The devices of the present invention may also provide for the remote application of specific and selective fields (e.g., application of a field at a distance from diseased or injured tissue), although it will be appreciated that capacitively coupled devices must touch the subject's skin. The devices of the present invention may include means for attaching the electrodes to the body of a patient in the vicinity of injured or diseased tissue in the case of capacitive coupling. For example, as shown in FIG. 8, self-adherent conductive electrodes may be attached to the skin of the patient on both sides of a fractured bone 18 or joint 20. The device of the present invention may include self-adherent electrodes for attaching the device to the body of a patient. For example, the device 10 of the present invention may include electrodes 12 attached to a power unit 14 that has a VELCRO® patch 16 on the reverse side such that the power unit 14 can be attached to a VELCRO® strap (not shown) fitted around a cast on the patient. In the case of inductive coupling, the device of the present invention may include coils or solenoids connected to a power unit in place of electrodes.

The device 10 of the present invention can be employed in a variety of ways. The device 10 may be portable or may be temporarily or permanently attached to a patient's body. The device 10 of the present invention is preferably non-invasive. For example, the device 10 of the present invention may be applied to the skin of a patient by application of electrodes 12 adapted for contact with the skin of a patient for the application of fields generated by the predetermined specific and selective signals. Such signals may also be applied via coils or solenoids (not shown) in which time varying currents flow, thus producing specific and selective electromagnetic fields that penetrate the tissue. The device 10 of the present invention may also be capable of implantation in a patient, including implantation under the skin for direct contact with the bone of a patient.

Those skilled in the art will further understand that the devices of the present invention can be provided in a variety of forms including a capacitively coupled power unit with programmed, multiple, switchable, specific and selective signals for application to one pair or to multiple pairs of electrodes, or electromagnetic coils or a solenoid attached to a power unit with switchable, multiple, specific and selective signals, and an ultrasound stimulator with a power supply for generating specific and selective signals. Generally speaking, device preference is based on patient acceptance and patient compliance. The smallest and most portable unit available in the art at the present time is a capacitive coupling unit; however, patients with extremely sensitive skin may prefer to use inductive coupling units. On the other hand, ultrasound units require the most patient cooperation, but may be desirable for use by certain patients.

EXAMPLE

The invention is demonstrated in the following example, which is for purposes of illustration and is not intended to limit the scope of the present invention.

Materials and Methods

MC3T3-E1 bone cells ($5 \times 10^5$ cells/cm$^2$) were plated onto specially-modified Cooper dishes. The cells were grown to seven days with the medium changed just prior to beginning of the experimental condition. The experimental cell cultures throughout these studies were subjected to a capacitively coupled 60 kHz sine wave signal electric field with an output amplitude of 44.81 V peak-to-peak. This produced a calculated-field strength in the culture medium in the dishes of 20 mV/cm with a current density of 300 µA/cm$^2$. Control cell culture dishes were identical to those of the stimulated dishes except that the electrodes were not connected to a function generator.

At the end of the experiment, total RNA was isolated using TRIzol, according to the manufacturer's instructions, and reversed transcription (RT) using SuperScript II reverse transcriptase was performed. Oligonucleotide primers to be used in the real time RT-PCR technique were selected from published cDNA sequences or designed using the Primer Express software program. Quantitative real-time analysis of RT-PCR products was performed using an ABI Prism® 7000 Sequence Detection System.

Figure 1:
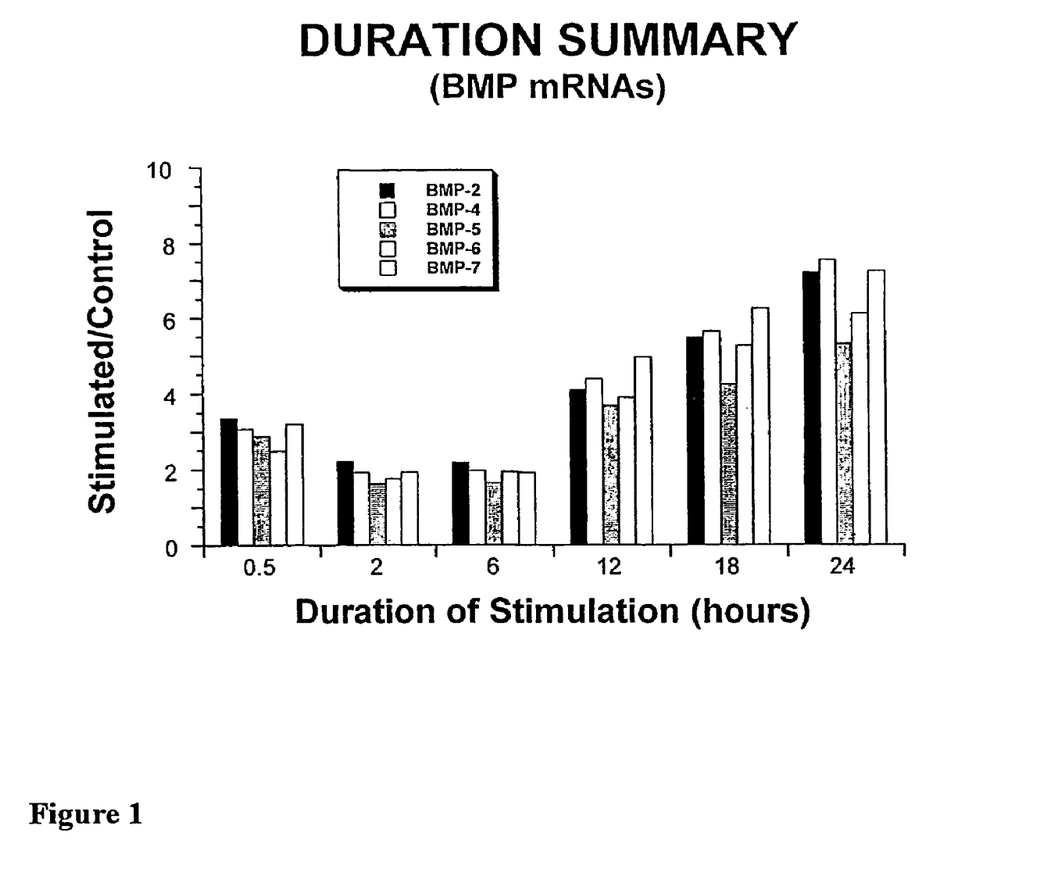
FIG. 1 is a graphic representation of the mRNA expression of BMP-2, BMP-4, BMP-5, BMP-6, and BMP-7 when bone cells are exposed to a 20 mV/cm capacitively coupled electric field for various time durations. As indicated, the maximum expression for the various BMP mRNAs occurred with a signal of 24 hours duration.
Figure 2:
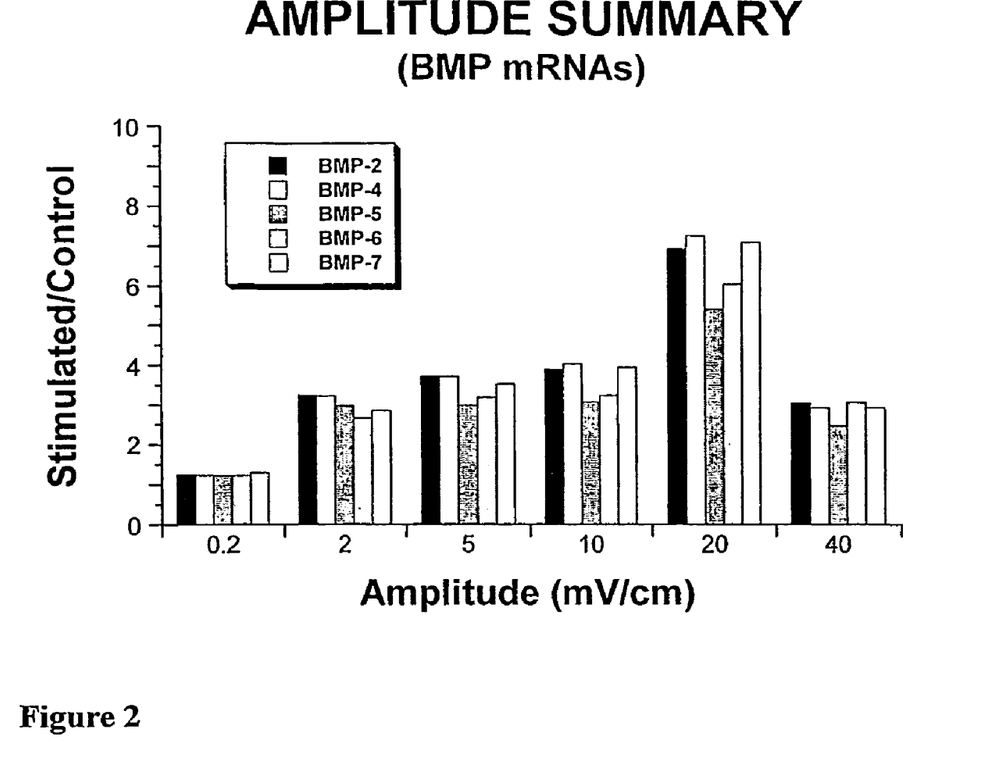
FIG. 2 is a graphic representation of mRNA expression of BMP-2, BMP-4, BMP-5, BMP-6, and BMP-7 when bone cells are exposed to various capacitively coupled electric field amplitudes with a duration of 24 hours. As indicated, the maximum expression for the various BMP mRNAs occurred with a field amplitude of 20 mV/cm.
Figure 3:
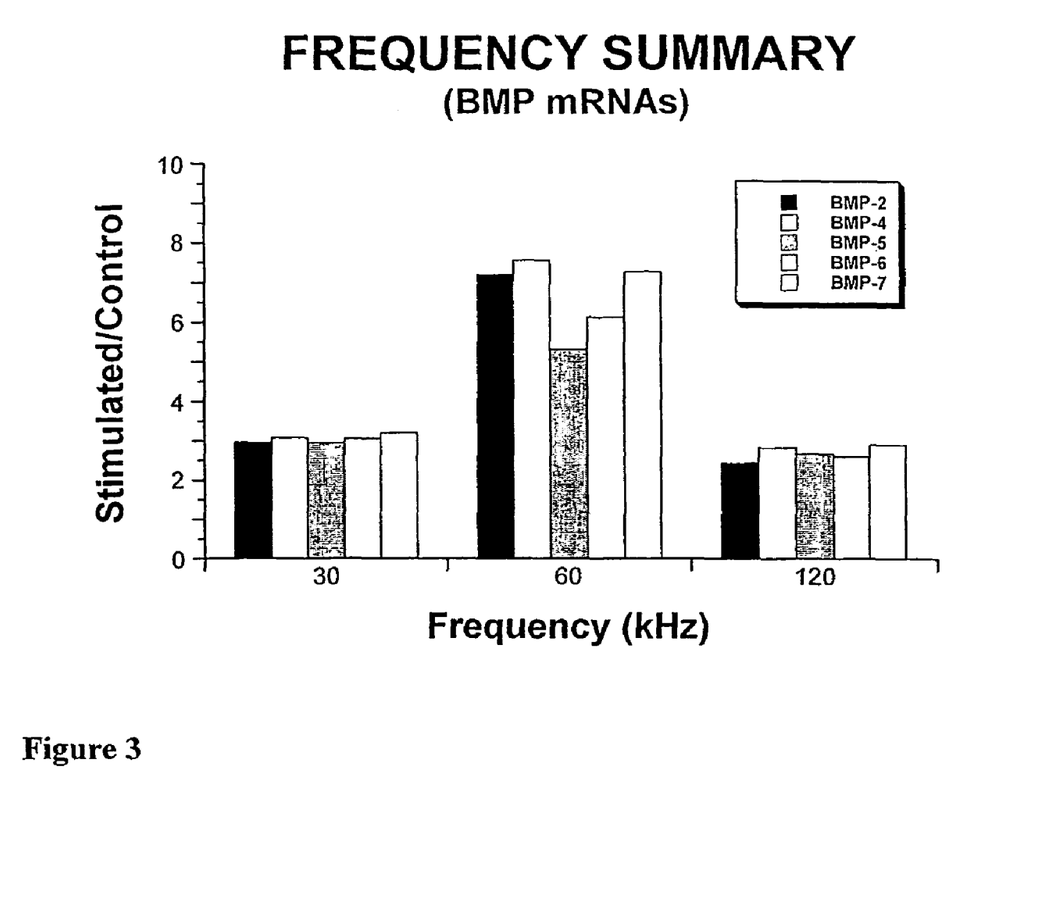
FIG. 3 is a graphic representation of mRNA expression of BMP-2, BMP-4, BMP-5, BMP-6, and BMP-7 when bone cells are exposed to various capacitively coupled electric field frequencies with a field amplitude of 20 mV/cm and a signal duration of 24 hours. As indicated, the maximum expression for the various BMP mRNAs occurred with a frequency of 60 kHz.
Figure 4:
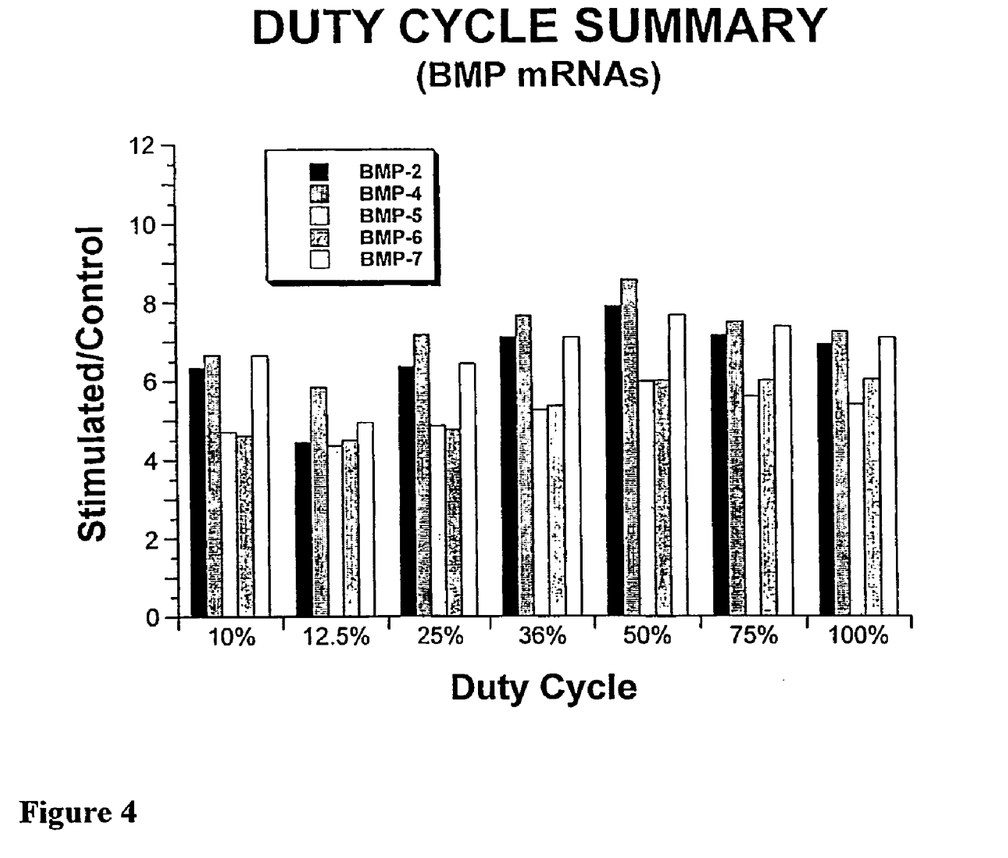
FIG. 4 is a graphic representation of mRNA expression of BMP-2, BMP-4, BMP-5, BMP-6, and BMP-7 when bone cells are exposed to various capacitively coupled electric field duty cycles with a frequency of 60 kHz, a field amplitude of 20 mV/cm, and a signal duration of 24 hours. As indicated, the maximum expression for the various BMP mRNAs occurred with a 50% duty cycle.
Figure 5:
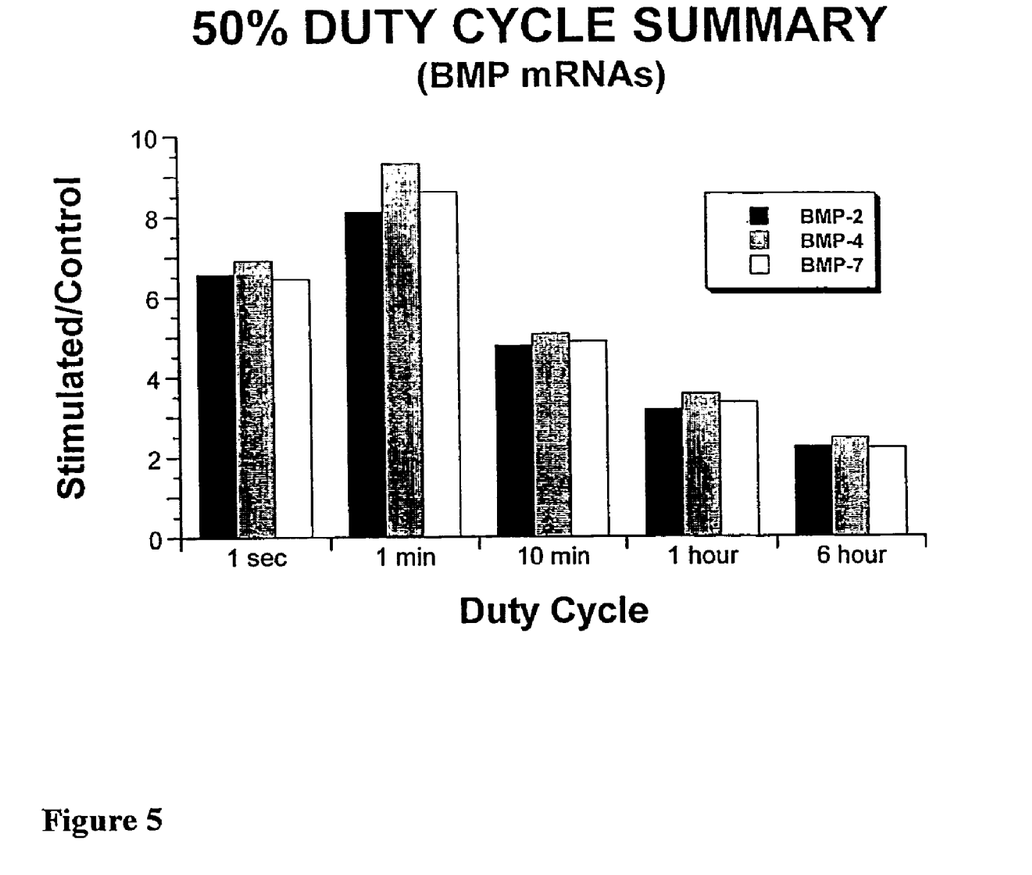
FIG. 5 is a graphic representation of mRNA expression of BMP-2, BMP-4, BMP-5, BMP-6, and BMP-7 when bone cells are exposed to a capacitively coupled electric field of a 50% duty cycle of various on-off times with a field amplitude of 20 mV/cm and a frequency of 60 kHz. As indicated, the maximum expression for the various BMP mRNAs occurred with a 1 minute ON/1 minute OFF 50% duty cycle.

The optimal signal for the desired up-regulation of (BMP) genes—including genes for BMP-2, BMP-4, BMP-5, BMP-6, and BMP-7, among others—was found systematically as follows. An electrical signal known to increase (or even just suspected to increase) cellular production of a given protein (e.g., 60 kHz sine wave) is taken as the starting signal for determining the specific signal for generating the field for the gene expression (mRNA) of that protein. A dose-response curve is first performed by varying the duration of the signal while holding all the other signal characteristics constant (amplitude, duty cycle, frequency, and waveform) (FIG. 1). This determines the optimal duration of the starting signal for the gene expression of that protein. As indicated in FIG. 1, the maximum expression for the various BMP mRNAs occurred with a signal duration of 24 hours. A second dose-response curve is then performed, this time varying the amplitude of the electric field (in mV/cm) while holding the optimal duration and other signal characteristics constant (FIG. 2). As indicated, the maximum expression for the various BMP mRNAs occurred with a field amplitude of 20 mV/cm. A third dose response is performed, this time varying the signal frequency while holding constant the optimal duration and optimal amplitude as found previously (FIG. 3). As indicated, the maximum expression for the various BMP mRNAs occurred with a frequency of 60 kHz. A fourth dose-response is performed varying the duty cycle from 100% (constant) to 10% or less while holding constant the optimal duration, amplitude, and frequency as found previously (FIG. 4). As indicated, the maximum expression for the various BMP mRNAs occurred with a 50% duty cycle. Finally, a fifth dose-response is performed varying the time OFF/time ON parameters while keeping the duty cycle at 50% and the amplitude and frequency at 20 mV/cm and 60 kHz, respectively, as previously found (FIG. 5). As indicated, the maximum expression for the various BMP mRNAs occurred with a 1 minute ON/1 minute OFF 50% duty cycle.

By this method, an optimal signal is determined for producing the greatest increase in the gene expression of the various BMPs.

Figure 6:
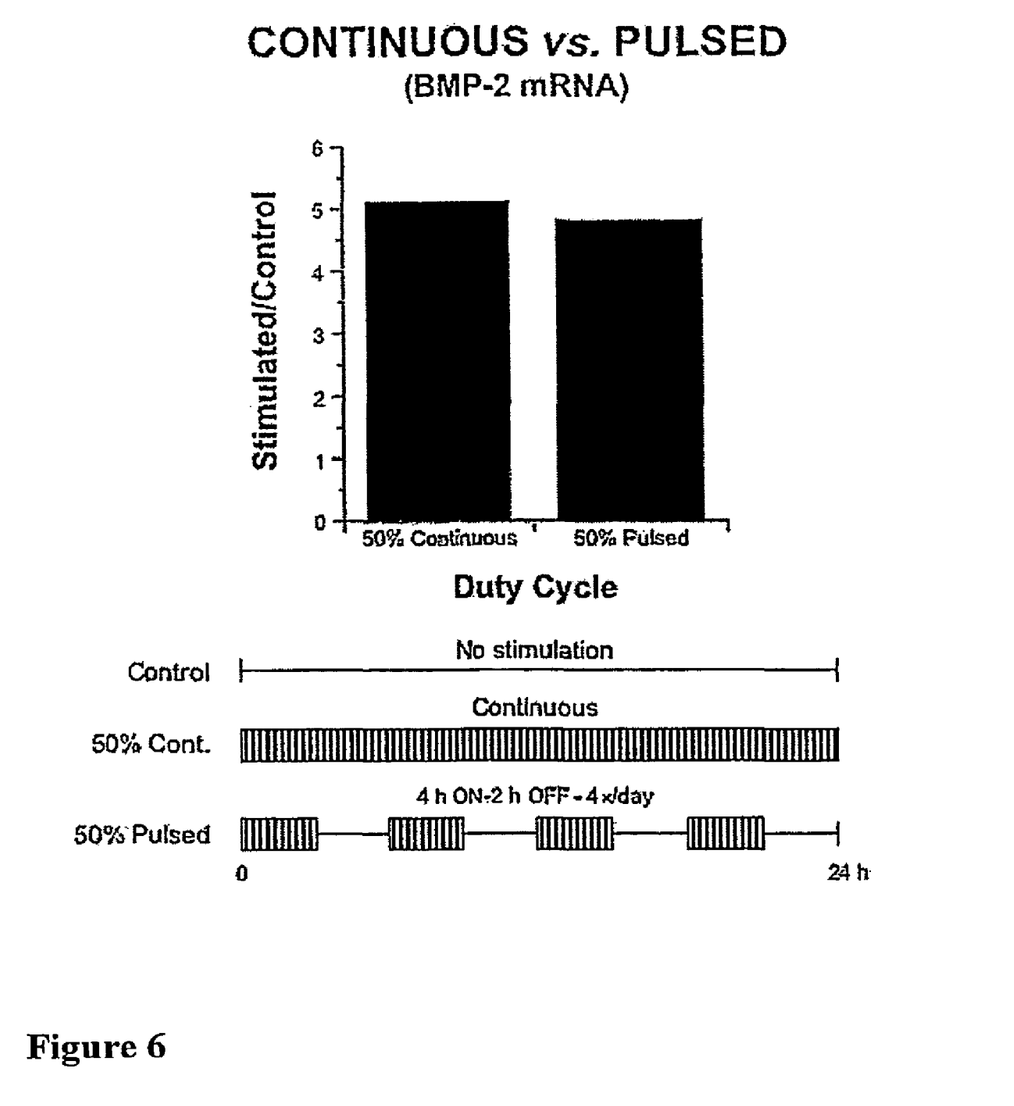
FIG. 6 is a graphic representation of BMP-2 mRNA expression when bone cells are exposed to a capacitively coupled continuous 50% duty cycle signal (20 mV/cm, 60 kHz, sine wave) versus a pulsed 50% duty cycle signal. As indicated, both signals showed essentially the same five-fold increase in BMP-2 mRNA.

A sixth experiment is performed comparing a continuous 50% duty cycle (capacitive coupling, 20 mV/cm, 60 kHz sine wave) to a pulsed 50% duty cycle (capacitive coupling, 20 mV/cm, 60 kHz). As indicated, the increase in BMP-2 mRNA was about 5 fold with each signal (FIG. 6).

Figure 7:
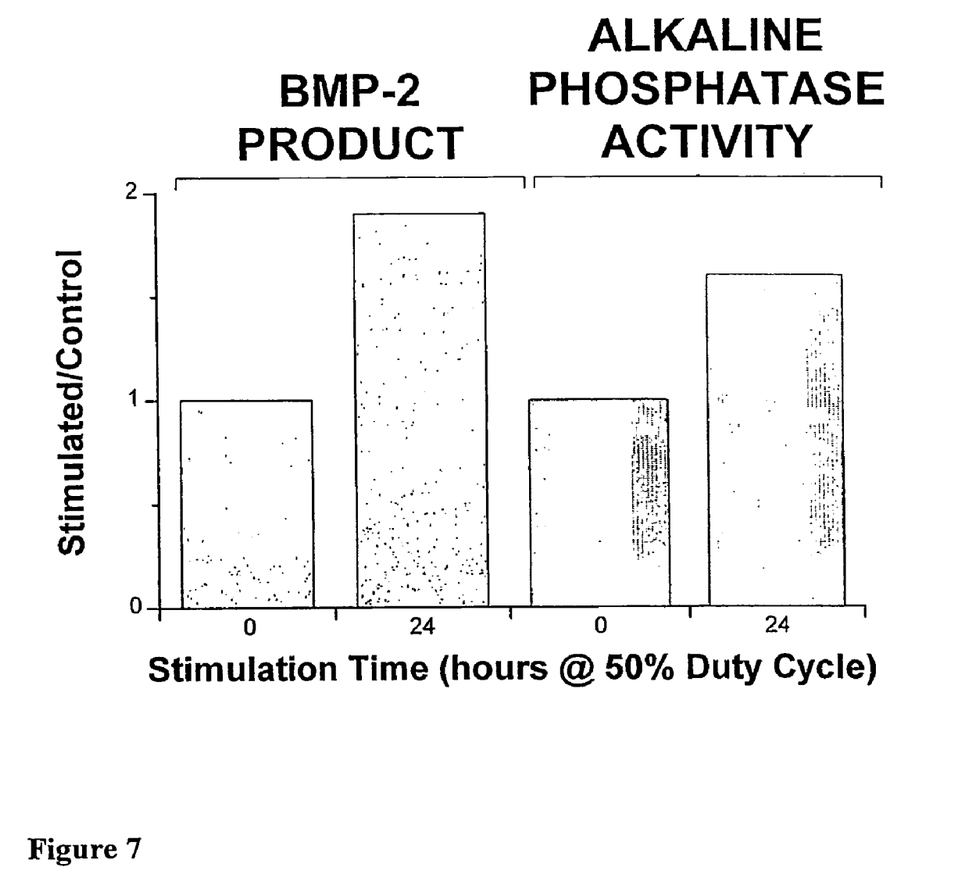
FIG. 7 is a graphic representation of BMP-2 protein production and alkaline phosphatase activity when bone cells are exposed to a 50% duty cycle, capacitively coupled signal (20 mV/cm, 60 kHz, sine wave) for 24 hours. As indicated, there was a 1.9 fold increase in BMP-2 production and a ⅙ fold increase in alkaline phosphatase activity.

A final experiment is performed to demonstrate an increase in production of the BMP mRNA product—namely, BMP-2 protein—as well as an increase alkaline phosphatase activity that can be induced by BMP-2 levels. After 24 hours of stimulation with a 50% duty cycle (capacitively coupled, 20 mV/cm, 60 kHz, sine wave) signal, there was a 1.9-fold and 1.6-fold increase in BMP-2 product and alkaline phosphatase activity, respectively (FIG. 7).

FIG. 8 illustrates a device 10 in accordance with the present invention that is used to treat a patient with osteoarthritis of the knee. As illustrated, two circular, soft conductive, self-adherent electrodes 12 are placed on the skin on either side of the knee at the level of the joint line 20. The electrodes 12 are attached to a power unit 14 that has a VELCRO® patch 16 on the reverse side such that the power unit 14 can be attached to a VELCRO® strap (not shown) fitted around the calf, thigh or waist. The electrodes 12 may be placed on the skin before the patient goes to bed each evening or any other convenient time. Of course, other suitable types of electrodes 12 may also be used.

The power unit 14 is preferably small (e.g., 6-8 ounces) and powered by a standard 9-volt battery to emit a 5-volt peak-to-peak, 6-10 mAmp, 20 mV/cm, 60 kHz sine wave signal to the electrodes 12 placed on the skin. When this signal is provided approximately 24 hours per day with the proper duty cycle (50%) in 1 minute ON and 1 minute OFF increments, it has been shown to significantly up-regulate genes encoding BMP.

The present invention clearly shows that the optimal electric field described in the example can very significantly up-regulate BMP-2, BMP-4, BMP-5, BMP-6, and BMP-7 mRNA and, hence, increase bone formation. Those skilled in the art will appreciate that an appropriate electric field, as described herein with capacitive coupling, is also equally effective with inductive coupling and all electromagnetic systems that produce equivalent, or nearly equivalent, electric field characteristics. Those skilled in the art will also appreciate that more unique signal characteristics may be discovered through more experimentation with more data points (e.g., a 100±3% duty cycle for 30±3 min), but such relatively minor variations in each of the signal characteristics are believed to be within the level of those skilled in the art given the teachings herein.

Those skilled in the art will also appreciate that numerous other modifications to the invention are possible within the scope of the invention. For example, the optimal field described herein can be applied to any bone via two or more appropriate surface electrodes, in pairs or strips, incorporated in braces, wraps, or casts, and delivered by means of capacitive coupling. Also, the optimal field described here can be applied to any bone via coil(s) or solenoid incorporated into braces, wraps, or casts, and delivered by means of inductive coupling. Accordingly, the scope of the invention is not intended to be limited to the preferred embodiment described above, but only by the appended claims.

What is claimed:

1. A method of up-regulating the gene expression of bone morphogenetic protein-2 (BMP-2) in targeted tissue, comprising the steps of:

generating at least one specific and selective signal having a frequency from 30 kHz to 120 kHz that when applied to a field generating device operatively disposed with respect to said targeted tissue causes the generation of a field having an amplitude of about 2 to 40 mV/cm in the targeted tissue that is specific and selective for the up-regulation of the gene expression of BMP-2 in said targeted tissue as measured by mRNA when said field is applied to the targeted tissue containing said BMP-2; and exposing the targeted tissue to the specific and selective field generated by said field generating device upon application of said at least one specific and selective signal thereto for a predetermined duration of time from approximately ½ hour to 24 hours per 24 hour period at a predetermined duty cycle from approximately 10%-100% so as to selectively up-regulate the gene expression of BMP-2 in said targeted tissue as measured by mRNA.

2. The method of claim 1 wherein the generating step comprises the step of selectively varying the amplitude from about 2 to 40 mV/cm, duration from approximately ½ hour to 24 hours per 24 hour period, duty cycle from approximately 10%-100%, frequency from 30 kHz to 120 kHz, and waveform of the specific and selective signal until the gene expression of BMP-2 in said targeted tissue as a result of exposure to the resultant specific and selective field as measured by mRNA in the targeted tissue is increased.

3. The method of claim 1 wherein said generating step comprises the step of generating the specific and selective signal at a remote source and said exposing step comprises the step of applying the field generated by the field generating device upon application of said specific and selective signal thereto to the targeted tissue.

4. The method of claim 3 wherein the exposing step comprises the step of applying the specific and selective signal to at least one electrode, at least one coil, or a solenoid located near the targeted tissue.

5. The method of claim 4 wherein the exposing step comprises the step of applying the field generated by the field generating device upon application of said specific and selective signal thereto to the targeted tissue through one of capacitive coupling and inductive coupling.

6. The method of claim 5 wherein when the specific and selective signal is applied to said at least one electrode, said at least one electrode generates a capacitive coupling electric field, and when the specific and selective signal is applied to the at least one coil or solenoid, said at least one coil or solenoid generates an electromagnetic field or a combined field.

7. A method for treating at least one of a bone fracture, fracture at risk, delayed union, nonunion, bone defect, spine fusion, osteonecrosis, and osteoporosis, comprising the steps of:
generating at least one specific and selective signal having a frequency of 30 kHz to 120 kHz that when applied to a field generating device operatively disposed with respect to targeted tissue causes the generation of a field having an amplitude of about 2 to 40 mV/cm in the targeted tissue that is specific and selective for the up-regulation of the gene expression of bone morphogenetic protein-2 (BMP-2) in said targeted tissue as measured by mRNA when said field is applied to the targeted tissue containing said BMP-2; and
exposing the targeted tissue to the specific and selective field generated by said field generating device upon application of said at least one specific and selective signal thereto for a predetermined duration of time from approximately ½ hour to 24 hours per 24 hour period at a predetermined duty cycle from approximately 10%-100% so as to selectively up-regulate the gene expression of bone morphogenetic protein in said targeted tissue as measured by mRNA.

8. The method of claim 7 wherein the exposing step comprises the step of capacitively coupling or inductively coupling the specific and selective field to the targeted tissue.

9. The method of claim 7 wherein the exposing step comprises the step of applying one of an electromagnetic field and a combined field to the targeted tissue.

10. The method of claim 7 wherein the generating step comprises the step of generating an electric signal having a sine wave configuration, a duty cycle of approximately 50%, and a frequency of approximately 60 kHz, where the resultant specific and selective field has an amplitude of approximately 20 mV/cm in the targeted tissue.

11. The method of claim 10 wherein the exposing step comprises the step of applying the specific and selective field to the targeted tissue for a duration of approximately 24 hours in a 24 hour period.

12. The method of claim 11 wherein the exposing step comprises the step of applying the specific and selective field to the targeted tissue for a 50% duty cycle of 1 minute ON and 1 minute OFF.

13. The method of claim 7 wherein the generating step comprises the steps of selectively varying the amplitude from about 2 to 40 mV/cm, duration from approximately ½ hour to 24 hours per 24 hour period, duty cycle from approximately 10%-100%, frequency from 30 kHz to 120 kHz, and waveform of the specific and selective signal until the up-regulation of the gene expression of BMP-2 as measured by mRNA in the targeted tissue by the resultant generated field is increased.

14. A device for the treatment of at least one of bone fractures, fractures at risk, delayed unions, nonunions, bone defects, spine fusion, osteonecrosis, and osteoporosis, comprising a signal source that generates at least one specific and selective signal having a frequency of 30 kHz to 120 kHz and a field generating device connected to the signal source so as to receive said at least one specific and selective signal and that is operatively disposed with respect to targeted tissue, said field generating device upon receipt of said at least one specific and selective signal causing the generation of a field having an amplitude of about 2 to 40 mV/cm in the targeted tissue that is specific and selective for the up-regulation of the gene expression of bone morphogenetic protein-2 (BMP-2) in the targeted tissue as measured by mRNA, said signal source controlling and varying duration of time of application of said at least one specific and selective signal for a predetermined duration of time from approximately ½ hour to 24 hours per 24 hour period and controlling and varying the duty cycle of said at least one specific and selective signal from approximately 10%-100% so as to selectively up-regulate the gene expression of BMP-2 in said targeted tissue as measured by mRNA as a result of application of the specific and selective field in said targeted tissue.

15. The device of claim 14 further comprising a portable power unit that drives said signal source.

16. The device of claim 14 further comprising means for attaching the field generating device to the body of a patient in the vicinity of bone tissue.

17. The device of claim 14 further comprising means for attaching the signal source to the body of a patient.

18. The device of claim 14 wherein the field generated by application of said at least one specific and selective signal to the field generating device is applied to said targeted tissue via one of capacitive coupling and inductive coupling.

19. The device of claim 18 wherein the specific and selective signal has a sine wave configuration, a duty cycle of approximately 50%, and a frequency of approximately 60 kHz, where the resultant specific and selective field has an amplitude of about 20 mV/cm in the targeted tissue.

20. A method of determining a specific and selective signal that when applied to a field generating device cause the field generating device to generate an electric field in targeted tissue that up-regulates bone morphogenetic protein in the targeted tissue, comprising the steps of selecting a starting signal with a signal shape and frequency that when applied to said field generating device causes said field generating device to generate a field that is known to increase or suspected to affect cellular production of bone morphogenetic protein-2 (BMP-2), selectively varying a duration of application of said starting signal until a duration that provides a most significant increase in production of BMP-2 is found, selectively varying an amplitude of said starting signal until an amplitude that provides a most significant increase in production of BMP-2 is found, selectively varying a duty cycle of the starting signal until a duty cycle that provides a most significant increase in production of BMP-2 is found, and selectively varying the duration of an on-off interval of the duty cycle of the signal until an on-off interval that provides a most significant increase in production of BMP-2 is found.

21. A method as in claim 20, comprising the further steps of selectively varying a frequency and waveform of said starting signal, keeping other signal characteristics constant, until a greatest increase in the gene expression of BMP-2 as measured by mRNA is found.

22. The device of claim 14, wherein the field generating device comprises at least one electrode, at least one coil, or a solenoid.

23. A device for the treatment of at least one of bone fractures, fractures at risk, delayed unions, nonunions, bone defects, spine fusion, osteonecrosis, and osteoporosis, comprising a signal source that generates at least one specific and selective signal having a frequency of 30 kHz to 120 kHz and a field generating device connected to the signal source so as to receive said at least one specific and selective signal and that is operatively disposed with respect to targeted tissue, said field generating device upon receipt of said at least one specific and selective signal causing the generation of a field having an amplitude of about 2 to 40 mV/cm in the targeted tissue that is specific and selective for the up-regulation of at least one of the gene expression of bone morphogenetic protein-4, 5, 6, and 7 (BMP-4, BMP-5, BMP-6, and BMP-7, respectively) in the targeted tissue as measured by mRNA, said signal source controlling and varying duration of time of application of said at least one specific and selective signal for a predetermined duration of time from approximately ½ hour to 24 hours per 24 hour period and controlling and varying the duty cycle of said at least one specific and selective signal from approximately 10%-100% so as to selectively up-regulate the gene expression of BMP-4, BMP-5, BMP-6, and/or BMP-7 in said targeted tissue as measured by mRNA as a result of application of the specific and selective field in said targeted tissue.

24. A method of determining a specific and selective signal that when applied to a field generating device cause the field generating device to generate an electric field in targeted tissue that up-regulates at least one of bone morphogenetic protein-4, 5, 6, and 7 (BMP-4, BMP-5, BMP-6, BMP-7, respectively) in the targeted tissue, comprising the steps of selecting a starting signal with a signal shape and frequency that when applied to said field generating device causes said field generating device to generate a field that is known to increase or suspected to affect cellular production of BMP-4, BMP-5, BMP-6, and/or BMP-7, selectively varying a duration of application of said starting signal until a duration that provides a most significant increase in production of BMP-4, BMP-5, BMP-6, and/or BMP-7 is found, selectively varying an amplitude of said starting signal until an amplitude that provides a most significant increase in production of BMP-4, BMP-5, BMP-6, and/or BMP-7 is found, selectively varying a duty cycle of the starting signal until a duty cycle that provides a most significant increase in production of BMP-4, BMP-5, BMP-6, and/or BMP-7 is found, and selectively varying the duration of an on-off interval of the duty cycle of the signal until an on off interval that provides a most significant increase in production of BMP-4, BMP-5, BMP-6, and/or BMP-7 is found.

* * * * *